(12) United States Patent
Murphy et al.

(10) Patent No.: US 8,187,883 B2
(45) Date of Patent: May 29, 2012

(54) METHOD AND SYSTEM FOR DELIVERING NUCLEIC ACID INTO A TARGET CELL

(75) Inventors: William L. Murphy, Madison, WI (US); Siyoung Choi, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 532 days.

(21) Appl. No.: 11/583,223

(22) Filed: Oct. 19, 2006

(65) Prior Publication Data

US 2007/0092906 A1 Apr. 26, 2007

Related U.S. Application Data

(60) Provisional application No. 60/729,131, filed on Oct. 21, 2005.

(51) Int. Cl.
 *C12N 15/00* (2006.01)
(52) U.S. Cl. ...................................... 435/455
(58) Field of Classification Search .................. None
 See application file for complete search history.

(56) References Cited

U.S. PATENT DOCUMENTS

| | | | |
|---|---|---|---|
| 6,890,556 B1 | 5/2005 | Segura et al. | |
| 7,266,457 B1 * | 9/2007 | Hickman | 702/19 |
| 2004/0121377 A1 * | 6/2004 | Ishii et al. | 435/6 |
| 2005/0090008 A1 | 4/2005 | Segura et al. | |

FOREIGN PATENT DOCUMENTS

WO WO 92/00995 * 1/1992

OTHER PUBLICATIONS

Yamauchi et al., Biochem Biophys Acta, Apr. 13, 2004, 1672: 138-147.*
Bamdad, Biophysical Journal, 1998: 1997-2003.*
Harrison et al., Nucl Acids Res, 1999, 27: i-v.*
Iyer et al., J Biol Chem, 1995, 270: 14712-14717.*
Cherng et al., Journal of Controlled Release,1999, 60: 343-353.*
Hosseinkhani et al., Current Pharmaceutical Biotechnology, 2003, 4: 109-122.*
Okahata et al., Anal. Chem., 1998, 70: 1288-1296.*
Hersel et al., Biomaterials, 2003, 24: 4385-4415.*
Sequence alignment.*
Demers L, et al., "A fluorescence-based method for determining the surface coverage and hybridization efficiency of thiol-capped oligonucleotides bound to gold thin films and nanoparticles," Anal. Chem. 72:5535-5541 (2000).
Ishihara T & Corey D, "Rules for strand invasion by chemically modified oligonucleotides," J. Am. Chem. Soc. 121:2012-2020 (1999).
Iyer M, et al., "Accelerated hybridization of oligonucleotides to duplex DNA," J. Biol. Chem. 270:14712-14717 (1995).
Segura T, et al., "Substrate-mediated DNA delivery: role of the cationic polymer structure and extent of modification," J. Control Release 93:69-84 (2003).
Yang F, et al., "The effect of incorporating RGD adhesive peptide in polyethylene glycol diacrylate hydrogel on osteogenesis of bone marrow stromal cells," Biomaterials 30:5991-5998 (2005).
Segura T, et al., "DNA delivery from hyaluronic acid-collagen hydrogels via a substrate-mediated approach," Biomaterials 26:1575-1584 (2005).

* cited by examiner

*Primary Examiner* — Ileana Popa
(74) *Attorney, Agent, or Firm* — Armstrong Teasdale LLP

(57) ABSTRACT

Controlled delivery of nucleic acid into target cells is achieved by immobilizing the nucleic acid and the cells to a substrate. Improved control over delivery is achieved by immobilizing the nucleic acid to the substrate via complementary DNA binding interactions with an oligonucleotide linker.

23 Claims, 5 Drawing Sheets

A.

B.

C.

A.

B.

A.

B.

METHOD AND SYSTEM FOR DELIVERING NUCLEIC ACID INTO A TARGET CELL

CROSS-REFERENCE TO RELATED APPLICATIONS

This application claims the benefit of U.S. Provisional Patent Application No. 60/729,131, filed Oct. 21, 2005, incorporated herein by reference as if set forth in its entirety.

STATEMENT REGARDING FEDERALLY SPONSORED RESEARCH OR DEVELOPMENT

Not applicable.

BACKGROUND

The present invention relates to methods and systems for delivering a nucleic acid molecule into a target cell, and more particularly to methods and systems for delivery with spatial or temporal control, or both.

While the nucleic acid delivery methods and systems of the invention apply generally to target cells capable of taking up nucleic acid from outside the cells, spatial and temporal control offers particular utility when applied in the context of cell differentiation, especially in bioengineering three-dimensional matrices such as tissues or organs containing multiple differentiated cell types that derive from a single stem cell precursor. Early strategies for directed cell differentiation focused on supplementing culture environments with growth factors, signaling molecules and extracellular matrix components. The interplay among target cells (especially stem cells), growth factors, signaling molecules and extracellular matrix components has shed light on the factors and conditions required to produce differentiated cells in sufficient numbers for regenerating a tissue of interest. More recent nucleic acid delivery strategies involve introducing nucleic acid molecules that encode the required factors, molecules and/or extracellular matrix components into cells.

Recent publications have reported limited spatial and/or temporal control over nucleic acid delivery to a desired cell population in culture. For example, in U.S. Pat. No. 6,890,556 (Segura et al.) and in published US Patent Application No. 2005/0090008 (Segura et al.), each incorporated herein by reference as if set forth in its entirety, polyanionic residues of a nucleic acid molecule (DNA, RNA or oligonucleotide) interact strongly with a polycationic polylinker (polymer, protein, peptide or lipid) to form a nucleic acid-polylinker non-covalent complex. The complex is covalently or non-covalently tethered to a support substrate that also supports cell adhesion.

The system described in the above-noted documents provides some spatial and temporal control over nucleic acid delivery by controlling both the strength of the interactions between the nucleic acid and the polylinker, as well as the location of the complexes relative to the adhered cells. For example, one can control the density of the polylinker or of the tether on the substrate, or one can select a polylinker or a tethering agent having stronger or weaker binding characteristics, as described therein.

Several investigators have shown that co-localization of cells and plasmid DNA—via immobilization of plasmid DNA to cell culture substrates—substantially enhances gene uptake and transgene expression, both in vitro and in vivo. See Shen H, et al., "Surface-mediated gene transfer from nanocomposites of controlled texture," Nat. Mater. 3:569-574 (2004); Segura & Shea, supra; Segura T, et al., "Substrate-mediated DNA delivery: role of the cationic polymer structure and extent of modification," J. Control Release 93:69-84 (2003); Bengali Z, et al., "Gene delivery through cell culture substrate adsorbed DNA complexes," Biotechnol. Bioeng. 90:290-302 (2005); Chang F, et al., "Surfection: a new platform for transfected cell arrays," Nucleic Acids Res. 32:e33 (2004); Delehanty J, et al., "A comparison of microscope slide substrates for use in transfected cell microarrays" Biosens. Bioelectron. 20:773-779 (2004); Delehanty J, et al., "Transfected cell microarrays for the expression of membrane-displayed single-chain antibodies," Anal. Chem. 76:7323-7328 (2004); Kato K, et al., "Transfection microarray of nonadherent cells on an oleyl poly(ethylene glycol) ether-modified glass slide," Biotechniques 37:444-448, 450, 452 (2004); Bielinska A, et al., "Application of membrane-based dendrimer/DNA complexes for solid phase transfection in vitro and in vivo," Biomaterials 21:877-887 (2000); and Ziauddin J & Sabatini D, "Microarrays of cells expressing defined cDNAs," Nature 411:107-110 (2001). However, previous immobilization approaches typically use non-specific interactions that complicate immobilization of multiple distinct plasmids. Additionally, the affinity of the plasmid DNA for the substrate is typically very high (e.g., pM dissociation constants for avidin-biotin-based DNA immobilization) and not readily controllable. Because the existing systems use non-specific polyanionic-polycationic interactions to hold the nucleic acid in place, the systems offer no mechanism for sequence-specific nucleic acid patterning on the supporting substrate.

It is advantageous to exert greater and more flexible spatial and temporal control over inductive growth factor production, and to enable production of multiple growth factors in a controlled manner in a material that can appropriately support new tissue growth and development.

BRIEF SUMMARY

In one aspect, the invention relates to nucleic acid molecules tethered via oligonucleotide linkers (or handles) to a supporting substrate. The nucleic acid molecules are characterized as linear or circular molecules having at least one DNA sequence or RNA sequence to be advantageously introduced into recipient cells. The at least one nucleic acid sequence can encode a protein or a peptide, in which case upstream transcriptional and/or translational promoters can be provided upstream of the encoding sequence. The nucleic acid sequence can be a regulatory element that is advantageously introduced into the cell (e.g., can be a sequence that encodes a regulatory antisense RNA of interest). Each of the oligonucleotide linker and the nucleic acid molecule is characterized as having a sequence complementary to at least a portion of the other, the complementary portion being of sufficient length and sufficient sequence complementarity to non-covalently attach the nucleic acid molecule to the oligonucleotide linker. The strength of the non-covalent attachment established between the two varies with the length, GC-content and extent of non-complementarity (i.e. mismatch), if any, in the complementary portion. The oligonucleotide linker is further characterized as being covalently or non-covalently fixed or tethered to the supporting substrate. The substrate can be a solid surface such as a self-assembled monolayer (e.g., an alkenethiolate on a gold-coated glass slide) or can be a two-dimensional or three-dimensional, semi-solid substrate such as a hydrogel network. Notably, the substrate can contain one or more polymer, especially a biodegradable polymer.

In a related aspect, a cell culture system of the invention includes recipient cells adhered (specifically or non-specifically) to the substrate onto which the nucleic acid molecules are tethered.

In another related aspect, the spatial distribution of the tethered nucleic acid molecules on the substrate can be provided in a predetermined manner to provide spatial control over nucleic acid molecule delivery. The nucleic acid molecules can be tethered to the oligonucleotide linkers before, at the same time as, or after the cells are positioned on the substrate.

In another related aspect, the invention relates to a method for introducing the tethered nucleic acid molecule into the adhered cultured cells, the method including the step of exposing the nucleic acid molecules to the cells under conditions whereby the cells take up the nucleic acid molecules. It will be appreciated that the ability of the cells to take up the nucleic acid molecules can be promoted or impeded by adjusting the non-covalent affinity between the nucleic acid molecule and the oligonucleotide linker. In certain embodiments, the culture temperature can be varied within a range of temperatures consistent with cell survival. In certain embodiments, the culture pH can be varied to a pH above the pKa of the amine group on adenine, guanine and cytosine, but within a pH range consistent with cell survival. In certain embodiments, the non-covalent interactions between the nucleic acid molecule and the oligonucleotide linker can be reduced by exposing the culture to focused ultrasonic stimulation. In some embodiments, the interactions can be reduced by exposing the culture to a second nucleic acid molecule (or other agent) that competitively interacts more strongly with the linker than does the first nucleic acid molecule, thereby competitively inhibiting the interactions between the first nucleic acid and the linker. In some embodiments, a linkage (e.g., an ester linkage) established between the oligonucleotide linker and the substrate can be rendered labile, thereby releasing the nucleic acid molecule from substrate making it available for cellular uptake. The skilled artisan will appreciate that these and other coordinated or uncoordinated approaches to modulating the timing with which the nucleic acid molecules are made available to the cells can arise from, and can be advantageously controlled by, the aforementioned extent and nature of complementarity between the nucleic acid molecules and the oligonucleotide linkers.

In certain embodiments, the uptake of the nucleic acid molecules by the cells directs differentiation of the adhered cells. In some specific embodiments, the nucleic acid molecules contain sequences that encode vascular endothelial growth factor (VEGF) or transforming growth factor β (TFGβ). In some embodiments, the nucleic acid molecule transfer can direct angiogenesis. In some embodiments, a differentiated cell produced in the method can receive a second tethered nucleic acid molecule. Accordingly, one can advantageously coordinate repeated transfer of various tethered nucleic acid molecules into the cells to spatially and/or temporally direct multi-step differentiation of the cells down one or more distinct cell lineages.

A feature of the present invention is sequence-specific interaction between the tethered nucleic acid molecule and the oligonucleotide linker.

Another feature of the present invention is the ability to vary the affinity between the oligonucleotide linker and the nucleic acid molecule can be adjusted by varying the length and extent of the complementary portion shared by the two.

An advantage of the present invention is improved control over both the strength and specificity of the interaction between the tethered nucleic acid molecule and the oligonucleotide linker.

Another advantage of the present invention is improved transfection efficiency.

BRIEF DESCRIPTION OF THE DRAWINGS

The invention will be better understood and features, aspects and advantages other than those set forth above will become apparent when consideration is given to the following detailed description thereof. Such detailed description makes reference to the following drawings, wherein.

Figure 1:
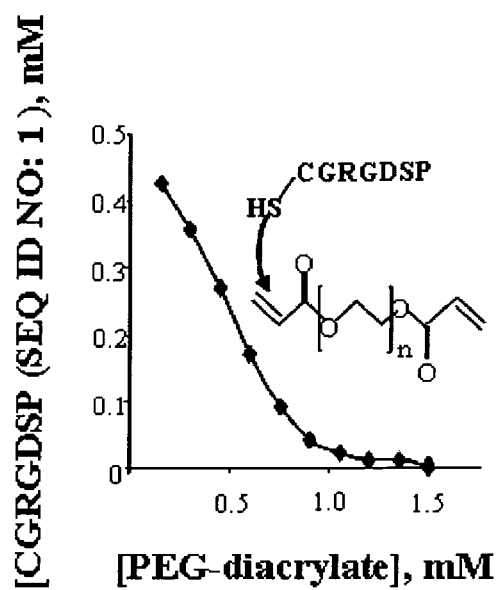
FIG. 1 shows a strategy for presenting covalently linked biomolecules on a poly(ethylene glycol) (PEG) hydrogel.

While the invention is susceptible to various modifications and alternative forms, specific embodiments thereof have been shown by way of example in the drawings and are herein described below in detail. It should be understood, however, that the description of specific embodiments is not intended to limit the invention to cover all modifications, equivalents and alternatives falling within the spirit and scope of the invention as defined by the appended claims.

DETAILED DESCRIPTION OF PREFERRED EMBODIMENTS

The invention includes methods and systems that employ nucleic acid molecules immobilized via complementary sequence interactions with an oligonucleotide linker to a substrate to transfect cells that are adhered to the substrate. The invention permits variation in the spatial patterns of the immobilized DNA to enable spatial control over nucleic acid molecule transfer. The invention also permits variation in the complementary DNA interactions to enable temporal control over transfer. References herein to "genes" are not intended to limit the scope of the invention to complete genes, but rather the term is intended to embrace any tethered nucleic acid molecule in a non-viral vector that can be delivered into a cell.

Short oligonucleotide linkers are used to sequester plasmid DNA on a substrate. The oligonucleotide linkers are small and chemically stable, and can therefore be covalently attached to materials and included into material patterning schemes without substantially influencing material properties.

The methods and systems of the present invention can, in principle, be used with many cell types including, but not limited to, stem cells, particularly hMSC.

The invention will be more fully understood upon consideration of the following non-limiting Examples.

EXAMPLES

Example 1

Development of Hydrogels for Cell Interaction

This example discloses the development and characterization of PEG hydrogels for use in directed cell differentiation.

Recent studies in tissue engineering and basic cell biology have focused on controlled presentation of signal to cells in a three-dimensional biomaterial matrix. These matrices are designed to present specific biomolecules on a background that does not interact with cells or proteins and are designed to allow for specific analysis and/or exploitation of a cell-ligand interaction. The substrate concurrently presents a cell adhesion ligand and an oligonucleotide linker for plasmid DNA immobilization to enhance gene uptake. The substrate disclosed herein is a PEG hydrogel that displays covalently attached oligonucleotides on a surface that is inert to interaction with cells and proteins.

As shown in FIG. 1, PEG chains derivatized with acrylate groups can react with sulfhydryl groups in cysteine-terminated peptides to form covalent conjugates. The resulting conjugates can then be photo-crosslinked into a hydrogel network. hMSC do not attach to PEG hydrogels alone, but attach and spread readily when PEG hydrogels are modified with an RGD ligand (CGRGDSP; SEQ ID NO: 1). Similarly, corneal epithelial cells attach and spread on PEG hydrogels presenting the RGD ligand. These cells, however, remained sparse and rounded on PEG hydrogels that were not modified with RGD ligand. PEG hydrogels can be coated not only with peptides, but also with covalently-linked rhodamine-labeled, thiol-terminated oligonucleotides. The ability to attach the oligonucleotide linkers provides a mechanism for controlled plasmid DNA immobilization described below.

The ability to quantify and control the concentration of oligonucleotide linkers that tether plasmid DNA or RNA (either anti-sense or siRNA) to the substrate is important for efficient transfection. Oligonucleotide linker concentration was measured on a gold surface. Oligonucleotide linkers (28mers) were mixed to varying extents (0%, 25%, 50%, 75% and 100%) with tri(ethylene glycol)-terminated alkanethiols. Following a twelve-hour incubation at room temperature, mercaptoethanol was used to displace oligonucleotide linkers from the surface to quantify immobilization. Demers L, et al., "A fluorescence-based method for determining the surface coverage and hybridization efficiency of thiol-capped oligonucleotides bound to gold thin films and nanoparticles," Anal. Chem. 72:5535-5541 (2000), incorporated herein by reference as if set forth in its entirety. Oligonucleotide linker concentration was quantified with an oligreen reagent (Invitrogen; Carlsbad, Calif.). Above about 40%, oligonucleotide linker density on the surface was not proportional to the percentage of oligonucleotide linkers in the mixture, even at different immobilization times.

Example 2

Engineering of Plasmid DNA for Interaction with Oligonucleotide Linker Sequences Typical protocols for non-viral transfection of mammalian cells employ plasmid vectors that are double-stranded and circular. Consequently, these plasmids do not contain single-stranded DNA sequences that can be targeted for controlled interaction with an immobilized oligonucleotide. To engineer a plasmid-oligonucleotide linker interaction, modified molecular biology techniques were used to confer a plasmid DNA expression vector with a single-stranded sequence. This sequence was then bound to a complementary oligonucleotide linker via DNA-DNA base pairing.

Figure 2:
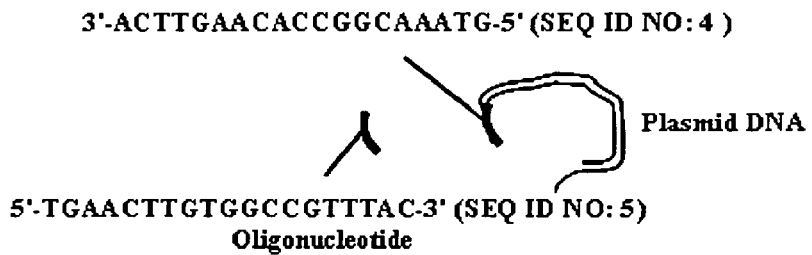
FIG. 2A-C show a strategy for engineering a plasmid to facilitate binding to an oligonucleotide linker on a support surface.
Figure 2:
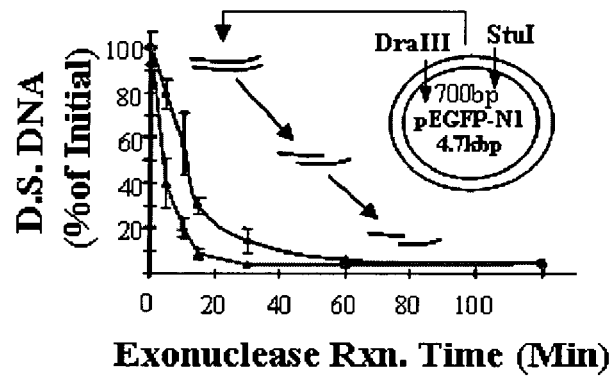
Figure 2:
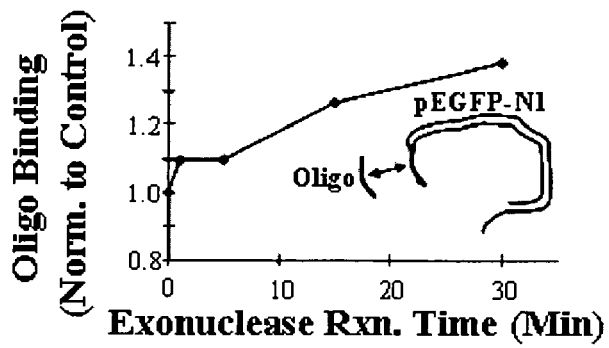

As shown in FIG. 2A, the approach first used an endonuclease to linearize a plasmid DNA vector, followed by brief treatment with a lambda exonuclease, which cuts double-stranded DNA in the 5' to 3' direction. The exonuclease cleaves only one strand, leaving a short (<50 bases), single-stranded sequence that is capable of interacting with a complementary single-stranded oligonucleotide linker. The rate of exonuclease cleavage was characterized by cutting a pEGFP-N1 plasmid at the DraIII and StuI restriction sites, which gave a shorter (~700 bp), double-stranded sequence. This shorter length facilitated the use of dyes to quantify double-stranded DNA and thus, exonuclease activity.

As shown in FIG. 2B, lambda exonuclease was used for various times and temperatures (20° C. for the upper curve and 25° C. for the lower curve) to characterize the amount of double-stranded DNA remaining. Exonuclease activity was determined with a picogreen assay (Molecular Probes; Portland, Oreg.). The results show that the cut rate of the exonuclease is temperature dependent, as expected, and that the cut rate of the exonuclease is approximately 15 bases per minute at 20° C.

As shown in FIG. 2C, a brief exonuclease treatment (<50 bases cleaved) of the full plasmid sequence, followed by incubation in a solution containing an oligonucleotide that is complementary to the revealed single-stranded DNA sequence, resulted in binding of the oligonucleotide to the plasmid. These results are important, as they provide proof-of-concept for the use of complementary DNA interactions to immobilize engineered plasmid DNA on substrates presenting covalently-linked oligonucleotide linkers.

Although the examples below use single-stranded DNA molecules, it is contemplated that double-stranded DNA molecules, such as plasmids, can be used in their native form (i.e. circular). For example, oligonucleotide linkers can be provided with inverted repeat sequences that hybridize with plasmid DNA. Iyer, et al., "Accelerated hybridization of oligonucleotides to duplex DNA," J. Biol. Chem. 270:14712-14717 (1995); and Ishihara T & Corey D, "Rules for strand invasion by chemically modified oligonucleotides," J. Am. Chem. Soc. 121:2012-2020 (1999), each incorporated herein by reference as if set forth in its entirety. Using this technique, two oligonucleotide linkers of the following sequences were constructed to hybridize to inverted repeats in pEFGP-N1: (1) inverted repeat 19 mer, [SH]-GGATCTTCACCTAGATCCT (SEQ ID NO: 2) and (2) non-inverted repeat 24 mer, [SH]-TGAACCATCACCCTAATCAAGTTT (SEQ ID NO: 3). An optional —$(CH_2)_6$ group is added between the 5'-terminal thiol group and the oligonucleotide linker for immobilization to the substrate. In the experimental system described herein, both oligonucleotide linkers reacted with a functional group on the substrate, leading to immobilization to the surface of the substrate. Following incubation with circularized pEFGP-N1, only the immobilized oligonucleotide linkers having SEQ NO: 2 hybridized with pEFGP-N1. Conversely, the immobilized linkers having SEQ ID NO: 3 did not hybridize with pEFGP-N1. Furthermore, the amount of pEFGP-N1 binding increased when the density of oligonucleotide linkers having SEQ NO: 2 was increased on the substrate.

Example 3

Preliminary Transfection of Mesenchymal Stem Cells with Plasmid DNA In Vitro

This example discloses the transfection of hMSCs with a pEGFP-N1 plasmid (Clontech; Mountain View, Calif.) that was either circular or linearized via DraIII endonuclease cleavage. The plasmid DNA was complexed with three separate types of transfection reagents, each widely used to enhance non-viral transfection efficiency. Transfection efficiency was measure by expression of endothelial green fluorescent protein (EGFP). As shown in FIG. 3A (for circular plasmid DNA) and FIG. 3B (for linear plasmid DNA), these reagents included the following: (1) a synthetic, polycationic polymer (white bars) (JetPEI: Polyplus Transfection; Illkirch, France); (2) a cationic lipid reagent (black bars) (Effectene: Qiagen; Valencia, Calif.); and (3) an activated cationic dendrimer (striped bars) (Superfect: Qiagen). The results demonstrate that hMSCs can be readily transfected in culture. Additionally, the cationic lipid reagent Effectene provided optimal transfection efficiency. Furthermore, hMSCs can be transfected with linearized plasmid DNA, although circular plasmid DNA was more efficient. These results thereby provide guidelines for the development the proposed approach by demonstrating effective non-viral transfection of hMSCs with a gene enccoding EGFP.

Example 4 (Prophetic)

Figure 4:
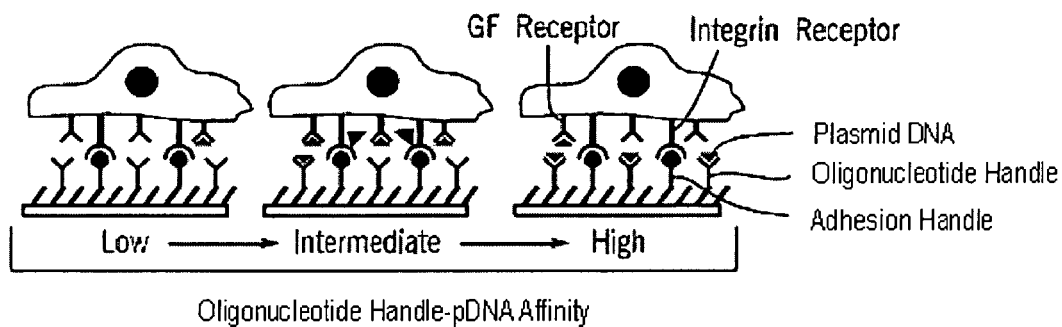
FIG. 4 shows a conceptualization of the immobilization scheme for transfection.
Figure 4:
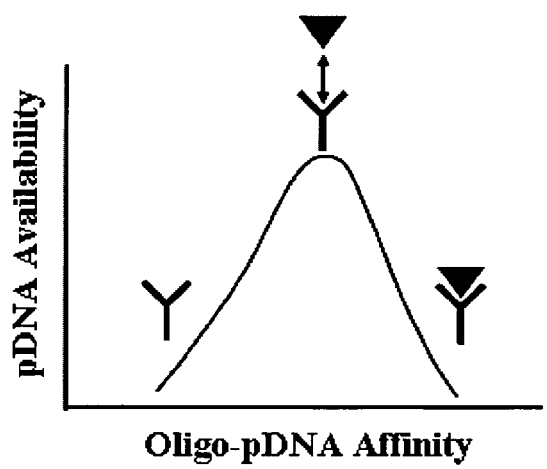

Synthesis of Hydrogels with Covalently-Linked Oligonucleotides and Cell Adhesion Peptides A. General Approach. As shown in FIG. 4A, one strategy to address the limitations of prior systems involves using an immobilization strategy that allows for facile variations in both the identity of the plasmid DNA immobilized to the substrate via the linker and the affinity of the plasmid DNA for the substrate. Complementary DNA interactions provide an ideal immobilization interaction to achieve these goals (FIG. 4B and Table 1). These interactions permit one to dictate the identity of an immobilized plasmid simply by displaying the appropiate complementary sequence on an oligonucleotide linker tethered to a substrate.

TABLE 1

Complimentary DNA Interactions.

| Complimentary Bases | $T_M$ (° C.) | $\Delta G$ (kcal/mol) | $K_D$ (M) |
| --- | --- | --- | --- |
| 30 | 72 | 43.4 | $25 \times 10^{-12}$ |
| 25 | 69 | 36.5 | — |
| 20 | 58 | 26.9 | $2 \times 10^{-9}$ |
| 15 | 49 | 19.3 | — |
| 10 | 30 | 9.6 | $1 \times 10^{-6}$ |

Another distinct advantage of this plasmid DNA immobilization approach is the intrinsic ability to control the affinity of a sequestering interaction. The properties of complementary DNA interactions are extremely well-characterized, and the strength of the interactions is dependent on the length of the complementary DNA sequences. Previous studies by Okahata et al. have demonstrated that the equilibrium dissociation constants ($K_D$) of DNA-DNA interactions vary from 1 µM for a 10 base pair interaction to 25pM for a 30 base pair interactions Okahata Y, et al., "Kinetic measurements of DNA hybridization on an oligonucleotide-immobilized 27-MHz quartz crystal microbalance," Anal. Chem. 70:1288-1296 (1998).

In the context of plasmid DNA sequestering, $K_D$=[O][P]/[OP] (where O represents an oligonucleotide sequence and P represents a plasmid containing a sequence complementary to O), and the $K_D$ is therefore the oligonucleotide concentration at which ½ of the soluble plasmid is bound to an oligonucleotide. Consequently, the aforementioned values for DNA-DNA $K_D$ indicate that it is possible to vary the availability of immobilized plasmid DNA by five orders of magnitude by simply varying the number of base pairs linking the DNA to the substrate from ten to thirty. The ability to systematically vary the availability of plasmid DNA enables substrate-mediated transfection to be optimized. In particular, high and low affinity immobilization results in sub-optimal gene uptake, but the method can be used to identify an intermediate affinity high enough to sufficiently bind plasmid DNA yet low enough to facilitate endocytosis by adjacent cells.

B. Methods. This section describes development of hydrogels that simultaneously bind plasmid DNA via complementary DNA (cDNA) interactions and bind cells via an RGD peptide ligand. The use of cDNA binding to immobilize plasmid DNA allows for controlled presentation of plasmids, as well as co-localization of plasmid DNA and target cells, as described above. For proper characterization of the fundamentals of this proposed approach, it is important to culture cells on substrates that: (1) are designed for cell attachment and plasmid DNA sequestering; (2) are translucent to facilitate analysis of attached cell activity; (3) are amenable to spatial patterning so that plasmid DNA presentation can be spatially controlled; and (4) are applicable to stem cell-based tissue regeneration schemes. Based on these criteria, PEG hydrogels as contemplated as the base material.

PEG-based hydrogels have found widespread use in tissue engineering applications due to their ease of processing and biocompatibility. Additionally, cells can be readily encapsulated within these gels during routine photo-crosslinking. However, cells exhibit little to no intrinsic adhesion or interaction with PEG hydrogels, and thus PEG provides an ideal "blank slate" upon which one can present specific biological molecules (e.g., peptide cell adhesion ligands and oligonucleotide linkers) in a controlled manner. A controlled presentation greatly facilitates an analysis of the fundamentals of gene delivery in this proposed system.

Simple chemistry can be used to covalently couple oligonucleotides and peptides to derivatized PEG molecules. These resulting polymer-biomolecule conjugates can then be photo-crosslinked to form three-dimensional hydrogel matrices. The ability to photo-crosslink these materials provides one with a means to spatially define the presence of oligonucleotides by photo-patterning of hydrogel matrices.

The translucence of these hydrogels facilitates examination of transfection and differentiation of attached cells. Taken together, these characteristics make PEG hydrogels a suitable substrate.

C. Synthesis of Hydrogels with Covalently-Linked Oligonucleotide Linkers and Cell Adhesion Peptides. It is advantageous to achieve control over location and concentration of oligonucleotides and peptides in a system that is robust and adaptable. To this end, hydrogels using a combination of covalent conjugation and photo-crosslinking are used.

Alcohol-terminated PEG chains are derivatized with acrylate groups via reaction with acryloyl chloride in benzene with triethylamine base, giving acrylate-terminated PEG chains. Reaction of these chains with oligonucleotides terminated on the 5'-end with a thiol group (5'-[SH]-TGAACCAT-CACCCTAATCAAGTTT-3'; SEQ ID NO:3) result in rapid and efficient Michael-type addition of the nucleophilic thiol to the electrophilic olefin in the acrylate group. This oligonucleotide sequence is complementary to one of the single-stranded sequences present in the engineered pEGFP-N1 plasmid described below.

Similarly, an RGD-containing, cysteine-terminated peptide (CGGRGDSP; SEQ ID NO:1) is linked to these PEG-diacrylate chains via the same Michael-type addition reaction. The RGD-containing peptide has a well-characterized ability to mediate cell adhesion through integrin receptor binding. Michael-type addition produces a covalent conjugate of PEG chains with oligonucleotides and peptides, and the ratio of oligonucleotide and peptide low (<0.1/1) concentration is maintained relative to the concentration of acrylate groups.

Because of the high concentration of PEG-diacrylate relative to oligonucleotide and peptide, the resulting solution contains copious unreacted acrylate termini capable of mediating photo-crosslinking into a network gel. To achieve the network gel, the PEG-peptide conjugates are mixed with a solution of 2-hydroxy-1-[4-(hydroxyethoxy)phenyl]-2-methyl-1-propanone photo-initiator (I2959: Ciba; Basel, Switzerland) and exposed to 365 nm UV radiation at 0.4 mW/cm2 via a handheld UV lamp to form photo-crosslinked network gels containing covalently bound oligonucleotide linkers and RGD-containing cell adhesion peptides. As demonstrated above, these hydrogel substrates mediate attachment and spreading of epithelial cells and hMSCs, and previous studies by others have indicated that PEG hydrogels presenting this concentration of RGD ligand also mediate attachment and proper function of mesenchymal stem cells. See Nuttelman C, et al., "In vitro osteogenic differentiation of human mesenchymal stem cells photoencapsulated in PEG hydrogels," J. Biomed. Mater. Res. 68A:773-782 (2004); and Anseth K, et al., "In situ forming degradable networks and their application in tissue engineering and drug delivery," J. Control Release 78:199-209 (2002).

The concentration of oligonucleotide linkers are defined—based on the total oligonucleotide included and the gel volume—and can be varied to optimize transfection, as described below.

D. Synthesis and Characterization of Engineered Plasmid DNA. Plasmid DNA vectors are typically double stranded and circular; therefore, they do not present single-stranded sequences that can interact with single-stranded oligonucleotide linkers. In addition, single-stranded M13 phage vectors have been shown to be inefficient in transfection experiments. Accordingly, the double-stranded DNA is modified to include single-stranded sequences capable of binding to oligonucleotides.

Figure 3:
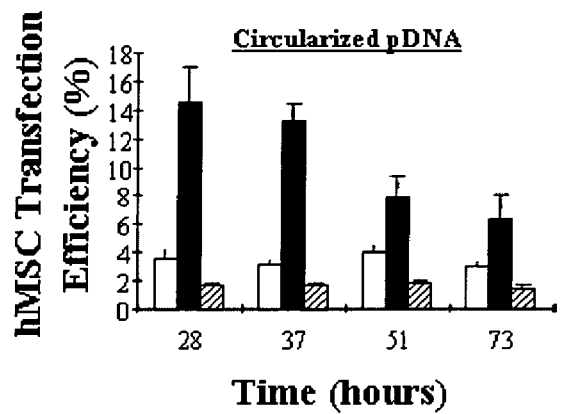
FIG. 3A-B shows optimization of transfecting circular or linear plasmid DNA into human mesenchymal stem cells (hMSC) using three transfection reagents.
Figure 3:
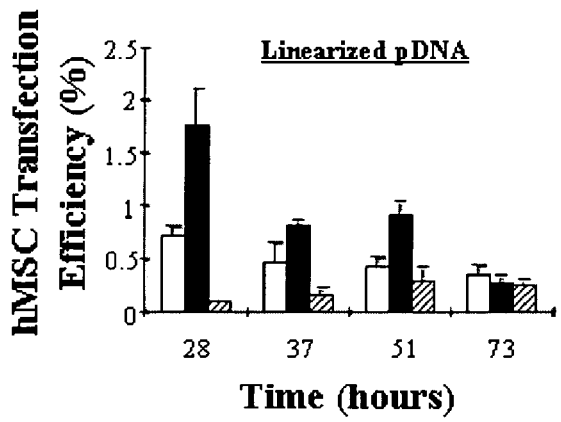

As described above, a combination of endonuclease and exonuclease treatment is employed to produce a pEGFP-N1 plasmid with short single-stranded overhangs. This plasmid encodes a gene for EGFP under the control of a mammalian CMV promoter. To create the engineered version of this plasmid, the circular plasmid is first linearized using a Dra III endonuclease. The linearized plasmid is treated with lambda exonuclease, which cuts in the 5' to 3' direction, to give overhangs on each end of the plasmid. The lambda exonuclease cuts this plasmid at a rate of approximately 15 nucleotides per minute at 20° C. Thus, the plasmid is reacted with exonuclease for three to four minutes followed by rapid deactivation of the exonuclease via addition of EDTA. Preliminary results confirm that linearized pEGFP-N1 can be used to transfect hMSCs (FIG. 3). The minimal exonuclease treatment described herein is not expected to have a substantial effect on transfection efficiency.

As noted above, oligonucleotide linkers can be constructed to hybridize to double-stranded DNA. Therefore, it is contemplated that double-stranded plasmid DNA vectors may be used.

E. Sequestering of Plasmid DNA on PEG Hydrogel Substrates. The PEG hydrogel substrates that present oligonucleotide linkers are combined with plasmid DNA molecules having single-stranded or double-stranded portions to immobilize the plasmid DNA. PEG hydrogels containing a covalently conjugated oligonucleotide linker are exposed to a solution containing an excess of the engineered pEGFP-N1 plasmid.

Plasmid-oligonucleotide binding is measured via fluorescence resonance energy transfer (FRET), using various fluorescent DNA labels (Molecular Probes; Mirus, Madison, Wis.). FRET provides an ideal measurement technique as it allows for sensitive quantitative measurement of molecular co-localization. The substrate-bound oligonucleotide linker is fluorescein labeled (donor fluorophore), and the engineered pEGFP-N1 plasmid is labeled with tetramethylrhodamine (acceptor fluorophore). Complete plasmid DNA binding to the oligonucleotide linker is then indicated by an increase in 570 nm emission (red light) and a disappearance of the 520 nm emission (green light). This shift results from an energy transfer from the fluorescein (bound to the oligonucleotide) to the tetramethylrhodamine (bound to the plasmid).

An increase in the donor fluorescence at 520 nm and a corresponding decrease in the acceptor fluorescence at 570 nm indicate removal of the pEGFP-N1 from the substrate, via cellular uptake or simply via release. This permits close monitoring of both plasmid DNA sequestering and plasmid DNA uptake, as described below. These fluorescent labels have a Forster radius of 55 Å, and are widely used in FRET analysis.

In each condition, the pEGFP-N1 plasmid is complexed with the Effectene transfection reagent after immobilization, as this reagent enhances transfection of hMSCs with pEGFP-N1.

Figure 5:
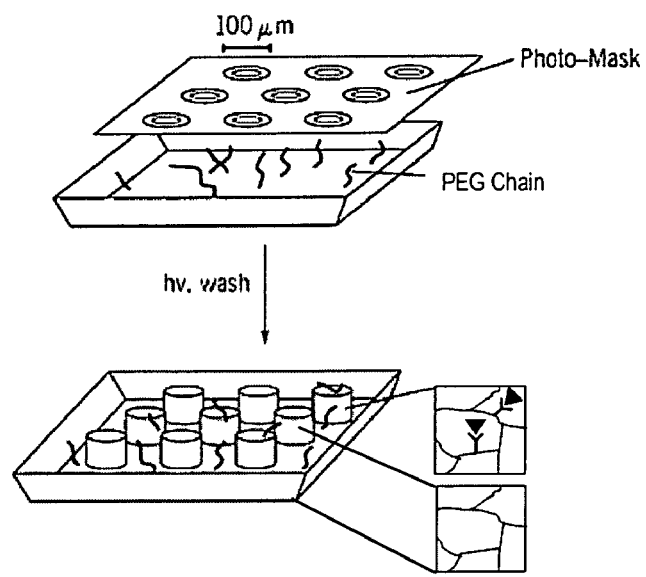
FIG. 5 shows a conceptualization for spatial patterning of plasmid DNA/oligonucleotide complexes.

F. Spatially Patterned immobilization of Plasmid DNA. Hydrogels with spatially-defined regions containing the oligonucleotide linker are created using patterned photo-crosslinking (FIG. 5).

Solutions of oligonucleotide-PEG conjugates are flowed into a glass chamber then exposed to long wavelength UV light through a photomask. The photomask is composed of linotype film, and includes an array of 100 μm diameter circular openings. Once the cylindrical pillars are photo-crosslinked, the remaining non-crosslinked solution is removed from the chamber and replaced with a solution that contains only PEG-diacrylate without bound oligonucleotide. The entire chamber is then exposed to UV radiation, resulting in crosslinking of a continuous hydrogel in which 100 mm diameter cylindrical pillars are capable of sequestering the pEGFP-N1 plasmid.

Patterned immobilization of plasmid DNA is monitored by fluorescent microscopy and FRET analysis, as described previously.

Example 5 (Prophetic)

Dependence of Transfection Efficiency on Plasmid DNA Availability and Cell Adhesion Characteristics A. General Approach: This section describes extensive characterization and optimization of hMSC transfection efficiency on PEG hydrogel substrates. As described above, the proposed approach for gene delivery involves co-localization of cells and plasmid DNA to the same substrate. This co-localization significantly enhances gene uptake.

Previous studies have demonstrated that substrate-mediated gene delivery provides more efficient transfection than soluble transfection, and these studies provide a strong, well-defined precedent for the proposed invention. However, previous studies have not examined the effects of DNA-substrate affinity on gene uptake, and it is likely that this affinity significantly influences the ability of cells to endocytose surface-immobilized plasmid DNA.

A recent non-viral gene delivery study indicated that the cell adhesion environment—including the identity and density of cell adhesion ligands—has a significant effect on gene uptake and transfection efficiency. Kong H, et al., "Non-viral gene delivery regulated by stiffness of cell adhesion substrates," Nat. Mater. 4:460-464 (2005). This effect was attributed to increased proliferation, which led to enhanced endocytosis of plasmid DNA. Based on these previous studies, and previous studies of hMSC activity on model substrates, the density of cell adhesion ligands is expected to strongly influence hMSC proliferation and nucleic acid molecule uptake.

Proper characterization of the influence of plasmid DNA-substrate affinity and cell adhesion characteristics on substrate-mediated gene uptake requires a gene delivery approach that enables: (1) control over plasmid DNA-substrate affinity, extending from very high affinity (pM) to rather low affinity (μM); (2) control over the amount of DNA immobilized on the substrate; and (3) control over the density of cell adhesion ligands presented to cells on the substrate. The system previously described is an ideal platform system to examine these fundamental aspects of substrate-mediated gene delivery.

B. Influence of Plasmid Concentration on Transfection of hMSCs. The concentration of plasmid DNA in solution is an important parameter during traditional transfection of cells with plasmid DNA, and it is expected that the amount of immobilized plasmid DNA is a similarly important parameter in substrate-mediated transfection. Modulating the density of oligonucleotide linkers covalently linked to the substrate can vary this concentration. Varying concentrations of a twenty-four base pair, thiol-terminated oligonucleotide linker (5'-[SH]-TGAACCATCACCCTAATCAAGTTT-3'; SEQ ID NO: 3) are reacted with PEG-diacrylate, as described above. This sequence length results in a high affinity immobilization (<1 nM dissociation constant) of plasmid, and thus a well-defined substrate immobilization density. However, based on the results of previous substrate-mediated DNA delivery studies, which have used similar interaction strengths (e.g., avidin-biotin interactions), it is expected that hMSCs can internalize the immobilized plasmid DNA.

The ratio of thiol-oligonucleotide to acrylate groups are varied from 1:100 to 20:100 to systematically vary the amount of immobilized plasmid DNA, hMSCs are added to the surface of these gels, and the cells are analyzed as described below. These substrates also present an RGD-containing peptide to mediate cell adhesion, and the RGD ligand can occupy 1% of the total acrylate groups. This RGD ligand density has been shown to promote attachment and proper function of hMSCs on PEG hydrogels. Yang F, et al., "The effect of incorporating RGD adhesive peptide in polyethylene glycol diacrylate hydrogel on osteogenesis of bone marrow stromal cells," Biomaterials 30:5991-5998 (2005).

The structure of the photo-crosslinked hydrogel should not be compromised by the reaction of terminal acrylate groups with oligonucleotides and peptides. Therefore, the equilibrium swelling ratios and the compressive moduli of hydrogels are prepared with variable amounts of linked oligonucleotides. Swelling is performed in PBS, and mechanical properties are measured using an Instron 3342 mechanical testing system (Instron Corp; Canton, Mass.). Any compromise in the physical properties of the hydrogels can be addressed by decreasing the degree of PEG-diacrylate conjugation to the oligonucleotide.

C. Influence of Plasmid DNA-Substrate Affinity on Transfection of hMSCs. DNA-DNA interactions are well-characterized, and the affinity of complementary DNA sequences can be varied from μM to pM equilibrium dissociation constants simply by changing the number of complementary bases from ten to thirty. The ability to systematically vary the affinity of plasmid DNA with a substrate is unique in the area of substrate-mediated transfection.

Hydrogel substrates presenting covalently immobilized oligonucleotide linkers with variable lengths (5, 10, 15, 20, 25 and 30 bases), and presenting an RGD-containing peptide for cell adhesion (1% ligand density), are created as described above. The oligonucleotide linker can be presented at a density that provides optimal transfection efficiency without compromising hydrogel structure. The actual concentration of immobilized DNA on these substrates can vary based on the affinity of the plasmid for the substrate, with this relation being determined as described below. Immobilized plasmid DNA can occupy each oligonucleotide linker having a length greater than fifteen bases, as these complementary plasmid DNA interactions can have a dissociation constant less than 10 nM. The plasmid DNA and oligonucleotide linker concentrations can each be greater than 100 nM.

D. Influence of Cell Adhesion Ligand Density on hMSC Proliferation, and Transfection. Previous studies suggest that the amount of plasmid DNA internalized can be dependent on proliferation and migration of several cell types. In particular, a recent study indicates that the density of cell adhesion ligands presented to cells in culture can significantly alter gene uptake, and this effect is attributed to differences in cell proliferation.

The approach provides an excellent platform system to examine and control the effects of cell adhesion ligand density on cell activity and gene delivery, as PEG hydrogels do not mediate cell attachment in the absence of covalently linked ligands. PEG hydrogels are created in which 0.1%-10% of the acrylate groups are occupied by an RGD-containing cell adhesion ligand. Cells are seeded onto these hydrogels (seeding density=3,000 cells/cm$^2$) and hMSC proliferation is analyzed using an assay for total DNA at two-day intervals for ten days, as described previously.

In parallel, gene uptake and transfection efficiency are characterized on substrates with these variable concentrations of RGD-containing peptide ligands. These substrates can also contain oligonucleotide linkers to sequester engineered pEGFP-N1. The oligonucleotide concentration and number of bases that provide optimal gene uptake and transfection can be selected as suitable conditions.

E. Characterization of hMSC Gene Uptake, Transfection Efficiency and Verification of Multipotential. To characterize and optimize the gene delivery approach both gene uptake and transgene expression are analyzed, as above. The immobilized plasmid DNA can be immobilized alone or complexed with the Effectene transfection reagent.

In this format, plasmid DNA immobilized on the substrate via complementary DNA interactions emits only red fluorescence, as a result of the energy transfer from the donor fluorescein (bound to the oligonucleotide) to the acceptor tetramethylrhodamine (bound to the plasmid). An increase in the donor fluorescence at 520 nm (green light) and a corresponding decrease in the acceptor fluorescence at 570 nm—as well as the presence of tetramethylrhodamine label within the bound hMSCs—indicate cell-mediated removal of the pEGFP-N1 from the substrate via endocytosis. Therefore, FRET can be used to quantify the amount of plasmid DNA that has been removed from the substrate, and imaging of fluorescence intensity at 570 nm provides a qualitative measure of gene uptake within cells.

To quantify gene uptake, cells are detached from the substrate after various time periods in culture and analyzed fluorometrically to quantify 570 nm fluorescence emission. To measure transfection efficiency cells are imaged in culture at twenty-four hour intervals and the number of cells expressing EGFP is characterized manually.

EGFP expression is also quantified using fluorometric analysis to determine the total amount of EGFP synthesis. If this technique is insufficiently sensitive to detect EGFP expression variations, a modification of the pEGFP-N1 plasmid, a plasmid that encodes luciferase under control of the pCMV promoter, such as the pEGFPluc plasmid, can be used. A standard assay for luciferase activity can then enable highly sensitive quantitative analysis of transgene expression. Taken together, these analyses provide definitive measures of both gene uptake and transgene expression.

Standard assays of hMSC multipotential involve exposing cells to specific culture environments and analyzing markers associated with osteogenesis, chondrogenesis and adipogenesis. Therefore, to initially confirm multilineage potential of hMSCs after substrate-mediated transfection, standard markers for osteogenic, chondrogenic, adipogenic and other differentiation can be evaluated using recommended procedures (available from Cambrex; East Rutherford, N.J.).

To induce differentiation toward the endothelial cell lineage, hMSCs can be cultured in low glucose DMEM with 2% fetal bovine serum and 50 ng/ml VEGF, conditions used previously to direct differentiation of hMSCs into endothelial cells. The analysis can include immunostaining and gene expression analysis of both early stage (CD31, Flk-1) and late stage (CD34, E-selectin, VE cadherin) markers of endothelial cell differentiation. Cell populations can be analyzed for expression of these markers at forty-eight hour intervals for ten days in culture, which has been shown to be an appropriate timeframe for analysis of endothelial cell differentiation from MSCs. RT-PCR primers can be designed as described in previous literature and relative quantification of signals can be achieved by normalizing to β-actin.

To induce differentiation into smooth muscle cells, hMSCs can be cultured in low glucose DMEM containing 10% fetal bovine serum and 10 ng/ml TGFβ1, conditions that induce differentiation down the smooth muscle cell lineage in two-dimensional culture.

Cells can be analyzed for expression of smooth muscle myosin heavy chain and α-smooth muscle actin at three-day intervals for fifteen days in culture using standard immunostaining reagents (Biocare Medical; Walnut Creek, Calif.) and RT-PCR primers described in previous literature.

F. Expected Results. These studies systematically delineate the effects of various parameters on substrate-mediated transfection of hMSCs, and set the stage for controlled production of inductive growth factors as described below. Each parameter can have a well-defined influence on plasmid DNA uptake and expression. Specifically: (1) an increase in the plasmid DNA concentration results in an increase in the level of gene uptake, and the amount of total transfection of hMSCs; (2) the affinity of plasmid DNA for the hydrogel substrate has a substantial effect on the level of gene uptake, thereby making it possible to optimize gene uptake by varying the plasmid DNA-substrate affinity; and (3) an increase in the density of RGD-containing cell adhesion ligands results in an increase in the rate of proliferation of hMSCs, thereby enhancing the uptake of immobilized pEGFP-N1. The increase in gene uptake, in turn, is expected to lead to greater transfection of hMSCs, as measured by increased production of EGFP in vitro. Based on these expected results, the level of hMSC transfection can be tailored by varying the concentration of immobilized plasmid DNA, the length of the oligonucleotide linker used for plasmid DNA immobilization, and the cell adhesion properties of the substrate.

Preliminary results indicate that linearized plasmid DNA can be used to transfect hMSCs. If transfection efficiency is low (<10% of cells in culture are EGFP+), an alternate expression vector (e.g., pNGVL-150) or transfection reagents (e.g. DEAE-dextran, lipofectamine) for plasmid DNA complexation can be employed.

Expression vectors similar to the pEGFP-N1 vector have been used previously to transfect hMSCs67, and we have determined that the Effectene transfection reagent allows for more efficient transfection of hMSCs relative to other cationic reagents, thus low transfection efficiency is not anticipated. However, variation in the reagents employed would not change the general approach to substrate-mediated transfection described.

The approach can also be used to immobilize circular DNA. Circular pEGFP-N1 DNA was melted at 98° C., then cooled to 37° C. and added to a solution containing a 10×-excess of an oligonucleotide complementary to one of the plasmid DNA strands. This procedure results in efficient binding of the oligonucleotide to the plasmid. These preliminary results demonstrate application of the approach to circular plasmid DNA immobilization as well. Further preliminary studies indicate that circular plasmid DNA enables more efficient transfection of hMSCs in culture.

Example 6 (Prophetic)

Spatially-Controlled Transfection of hMSCs with Genes Encoding Two Inductive Growth Factors: Vascular Endothelial Growth Factor and Transforming Growth Factor-β1

A. General Approach. The approach outlined above enables transfection of hMSCs with control over the location of transfection and the level of transgene expression (i.e. protein production). The following studies focus on exploiting the novel gene delivery approach to specifically control inductive growth factor production by hMSCs. The invention is ideally suited for vascular tissue regeneration by hMSCs for the following reasons: (1) because vascular tissue is a patterned, multicellular tissue and proper vascular tissue regeneration from stem cell precursors therefore requires spatial control over differentiation down multiple lineages; (2) because differentiation of hMSCs down the lineages that are relevant in vascular regeneration—endothelial and smooth muscle lineages—can be induced by the presence of specific growth factors—VEGF and TGFβ1; and (3) because successful induction of endothelial and smooth muscle cell differentiation, and consequent vascular tissue regeneration, must take place within a three-dimensional biomaterial matrix that supports new tissue development (e.g., a PEG hydrogel matrix).

B. Localized Transfection of hMSCs with Distinct Genes. Spatially patterned hydrogels are created using the method described above. These hydrogels present the RGD-containing cell adhesion ligand uniformly, but also present two different oligonucleotide linkers. The first linker is identical to the handle described above, and is designed to mediate immobilization of the pEGFP-N1 plasmid. The second linker is designed to mediate immobilization of the pDsRed2-N1 plasmid, engineered to contain a single-stranded sequence extending from the ClaI restriction site (rather than the DraIII site used in the pEGFP-N1). The pDsRed2-N1 plasmid is identical to the pEGFP-N1 plasmid, with the exception of the coding region, which contains the EGFP gene in pEGFP-N1 and the red fluorescent protein (RFP) gene in pDsRed2-N1. This strategy therefore enables immobilization of the plasmid via two separate mechanisms, and allows for patterning of two distinct genes on the same substrate. As described previously, spatially patterned transfection with these genes is characterized using fluorescence microscopy, and spatially-controlled emission of EGFP and RFP is observed.

C. Development of Plasmids Encoding VEGF and TGFβ1 and Analysis of Growth Factor Secretion. Plasmids are engineered to encode relevant inductive growth factors. IMAGE consortium clones containing the genes encoding VEGF-165 (clone #769910; ATCC, Rockville, Md.) and TGFβ1 (clone #59954; ATCC) are amplified using PCR and are cloned into the multiple cloning site of the pCI plasmid (Promega; Madison, Wis.) at the Xho1 and EcoR1 restriction sites to give pCIVEGF and pCITGFβ1. pCI has been used previously to induce production of human TGFβ1. Expression of these genes is under the control of the human CMV promoter in each plasmid, as in the case of EGFP and RFP gene expression, and is expressed in a manner similar to that of the GFP and RFP genes in the previous sections.

Production of VEGF and TGFβ1 by transfected hMSCs is initially analyzed on separate substrates. The pCIVEGF and pCITGFPβ1 plasmids are immobilized on PEG hydrogel substrates to direct transfection of adherent hMSCs using the methods described previously. As in the case of the pEGFP-N1 plasmid, the pCI plasmid is cut at DraIII site (at 1655), a unique restriction site far from the multiple cloning region of this plasmid. At twelve-hour time intervals after initiation of hMSC culture, the VEGF or TGFβ1 concentration in culture is analyzed using ELISAs for each of these proteins (Promega). The systematic studies performed in the previous section instruct these subsequent transfection studies, and the plasmid DNA concentration, plasmid DNA-substrate affinity, and cell adhesion environment are appropriately varied to demonstrate a high level of control over the amount of VEGF and TGFβ1 produced.

D. Expected Results. These studies are expected to produce a flexible and highly controlled method for delivery of genes encoding growth factors. Variation in the parameters enables control over the level of growth factor secretion by hMSCs. Furthermore, the methods described for patterning gene delivery allow for spatial control over growth factor secretion.

Stem cell differentiation is a dynamic field, and new mechanisms for induced differentiation of hMSCs are being actively developed. In addition, the effects of specific growth factors on hMSC differentiation are often complex, and context dependent. Therefore, despite the apparently well-characterized response of hMSCs to VEGF and TGFβ1, differentiation in this system may differ from previous protocols for hMSC differentiation down the endothelial and smooth muscle cell lineages. However, the approach is controllable and adaptable, allowing for regulation of the extent of transfection and the identity of the gene transferred into the cell. Consequently, the system can incorporate new protocols for growth factor-induced hMSC differentiation if necessary. The inherent flexibility of this approach therefore addresses the uncertainty typically associated with new approaches to direct stem cell differentiation.

Those of ordinary skill in the art will readily appreciate that the foregoing represents merely certain preferred embodiments of the invention. Various changes and modifications to the procedures and compositions described above can be made without departing from the spirit or scope of the present invention, as set forth in the claims below.

We claim:

1. A cell culture system comprising:
   a substrate;
   a nucleic acid molecule non-covalently attached to an oligonucleotide linker tethered to the substrate;
   a target cell capable of taking up the nucleic acid molecule by endocytosis, the cell being adhered to the substrate via a cell adhesion linker; and
   a culture medium compatible with survival of the target cell.

2. A culture system as recited in claim 1, wherein the substrate is selected from the group consisting of a polymeric hydrogel and a self-assembled monolayer.

3. A culture system as recited in claim 1, wherein the nucleic acid molecule is selected from the group consisting of a linear molecule and a circular molecule.

4. A culture system as recited in claim 1, wherein the oligonucleotide linker comprises an inverted repeat.

5. A culture system as recited in claim 1, wherein the target cell is a cultured stem cell.

6. A culture system as recited in claim 1, wherein the target cell is a cultured human cell.

7. A culture system as recited in claim 1, wherein the target cell is a cultured human stem cell.

8. A method for delivering nucleic acid into a target cell in a cell culture system, the system comprising a substrate, a nucleic acid molecule non-covalently attached to an oligonucleotide linker tethered to the substrate, a cell adhesion linker attached to the substrate and a target cell capable of taking up the nucleic acid molecule by endocytosis, the target cell being adhered to the substrate via the cell adhesion linker, and a culture medium compatible with target cell survival, the method comprising the step of:
   adjusting culture conditions of the cell culture system, such that the target cell takes up the nucleic acid molecule.

9. A method as recited in claim 8, wherein the substrate is selected from the group consisting of a polymeric hydrogel and a self-assembled monolayer.

10. A method as recited in claim 8, wherein the nucleic acid molecule is selected from the group consisting of a linear molecule and a circular molecule.

11. A method as recited in claim 8, wherein the oligonucleotide linker comprises an inverted repeat.

12. A method as recited in claim 8, wherein the target cell is a cultured stem cell.

13. A method as recited in claim 8, wherein the target cell is a cultured human cell.

14. A method as recited in claim 8, wherein the target cell is a cultured human stem cell.

15. A method as recited in claim 8, wherein the adjusting step includes the step of adjusting the culture temperature.

16. A method as recited in claim 8, wherein the adjusting steps includes the step of adjusting the culture pH.

17. A method as recited in claim 8, wherein the adjusting step includes the step of adding a competing nucleic acid molecule that competes with the attached nucleic acid molecule for complementary interaction with the oligonucleotide linker.

18. A method as recited in claim 8, wherein the adjusting step includes the step of stimulating the cell culture system with focused ultrasound.

19. A method as recited in claim 8, wherein the adjusting step includes the step of rendering labile a linkage between the linker and the substrate.

20. A culture system as recited in claim 1, wherein the cell adhesion linker comprises a RGD peptide.

21. A culture system as recited in claim 20, wherein the RGD peptide comprises SEQ ID NO: 1.

22. A method as recited in claim 8, wherein the cell adhesion linker comprises a RGD peptide.

23. A method as recited in claim 22, wherein the RGD peptide comprises SEQ ID NO: 1.

* * * * *

SEQUENCE LISTING

```
<160> NUMBER OF SEQ ID NOS: 5

<210> SEQ ID NO 1
<211> LENGTH: 7
<212> TYPE: PRT
<213> ORGANISM: Artificial
<220> FEATURE:
<223> OTHER INFORMATION: Synthetic peptide

<400> SEQUENCE: 1

Cys Gly Arg Gly Asp Ser Pro
1               5

<210> SEQ ID NO 2
<211> LENGTH: 19
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5'-terminal thiol group added

<400> SEQUENCE: 2
ggatcttcac ctagatcct                                              19

<210> SEQ ID NO 3
<211> LENGTH: 24
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
```

```
-continued

<222> LOCATION: (1)..(1)
<223> OTHER INFORMATION: 5'-terminal thiol group added

<400> SEQUENCE: 3
tgaaccatca ccctaatcaa gttt                                          24

<210> SEQ ID NO 4
<211> LENGTH: 19
<212> TYPE: DNA
<213> ORGANISM: Artificial
<220> FEATURE:
<223> OTHER INFORMATION: Synthetic oligonucleotide

<400> SEQUENCE: 4
gtaaacggcc acaagttca                                                19

<210> SEQ ID NO 5
<211> LENGTH: 19
<212> TYPE: DNA
<213> ORGANISM: Artificial
<220> FEATURE:
<223> OTHER INFORMATION: Synthetic oligonucleotide

<400> SEQUENCE: 5
tgaacttgtg gccgtttac                                                19
```